United States Patent [19]

Tsaur et al.

[11] Patent Number: 5,804,540
[45] Date of Patent: Sep. 8, 1998

[54] PERSONAL WASH LIQUID COMPOSITION COMPRISING LOW VISCOSITY OILS PRE-THICKENED BY NON-ANTIFOAMING HYDROPHOBIC POLYMERS

[75] Inventors: Liang Sheng Tsaur, Norwood; Mengtao He, Wayne, both of N.J.; Michael Massaro, Congers; Michael Paul Aronson, West Nyack, both of N.Y.

[73] Assignee: Lever Brothers Company, Division of Conopco, Inc., New York, N.Y.

[21] Appl. No.: 779,546

[22] Filed: Jan. 8, 1997

[51] Int. Cl.[6] ................ C11D 3/18; C11D 3/20; C11D 3/22; C11D 3/48
[52] U.S. Cl. ............ 510/135; 510/158; 510/159; 510/417; 510/463; 510/420; 510/437; 510/434; 510/475; 510/476; 510/131
[58] Field of Search ............... 510/135, 158, 510/159, 417, 463, 420, 437, 434, 475, 476, 131

[56] References Cited

U.S. PATENT DOCUMENTS

| | | | |
|---|---|---|---|
| 3,829,563 | 8/1974 | Barry et al. | 424/70 |
| 4,798,679 | 1/1989 | Castro et al. | 252/174.15 |
| 4,963,535 | 10/1990 | Sebag et al. | 514/54 |
| 5,221,534 | 6/1993 | DesLauriers et al. | |
| 5,308,526 | 5/1994 | Dias et al. | 252/125 |
| 5,346,642 | 9/1994 | Patel et al. | 252/174.21 |
| 5,389,305 | 2/1995 | Repinec et al. | 252/546 |
| 5,558,872 | 9/1996 | Jones et al. | 424/78.03 |
| 5,578,299 | 11/1996 | Starch | 424/78.03 |
| 5,653,970 | 8/1997 | Vermeer | 424/70.24 |
| 5,656,200 | 8/1997 | Boettcher et al. | 252/307 |
| 5,696,069 | 12/1997 | Ito et al. | 510/123 |
| 5,716,920 | 2/1998 | Glenn, Jr. et al. | 510/159 |

FOREIGN PATENT DOCUMENTS

| | | |
|---|---|---|
| 94/01084 | 1/1994 | WIPO . |
| 94/01085 | 1/1994 | WIPO . |
| 95/26710 | 10/1995 | WIPO . |
| 96/02224 | 2/1996 | WIPO . |
| 96/17591 | 6/1996 | WIPO . |
| 96/17592 | 6/1996 | WIPO . |
| 96/25144 | 8/1996 | WIPO . |
| 96/29979 | 10/1996 | WIPO . |

OTHER PUBLICATIONS

Derwent Abstract WO 94/17166.
Derwent Abstract WO 92/08444.
Derwent Abstract EP 578,481.
Soap/Cosmetics/Chemical Specialties, Feb., 1996, p. 24.

*Primary Examiner*—Douglas J. McGinty
*Attorney, Agent, or Firm*—Ronald A. Koatz

[57] ABSTRACT

The present invention relates to aqueous-based personal wash compositions comprising hydrophobic, low viscosity (less than 1000 cp) emollient agents which have been specifically pre-thickened with defined polymer composition. Use of the specific thickeners allow incorporation of the low viscosity oil (viscosity less than 1000 cp) in the personal wash compositions to deliver enhanced skin benefits and desired user properties without compromising foaming.

33 Claims, No Drawings

5,804,540

PERSONAL WASH LIQUID COMPOSITION COMPRISING LOW VISCOSITY OILS PRE-THICKENED BY NON-ANTIFOAMING HYDROPHOBIC POLYMERS

FIELD OF THE INVENTION

The present invention relates to liquid personal cleansing compositions comprising thickened low viscosity oils as moisturizing agents. More specifically, by thickening these low viscosity oils (i.e., oils having viscosity less than 1000 centipoise (cp)) with specific, oil mixable, hydrophobic polymers with a low degree of crystallinity, it is possible to deliver higher amounts of the oil to the skin/substrate from skin cleanser compositions without sacrificing foaming benefits. In this way, the advantages of these low viscosity oils can be effectively delivered. In addition, the oils thickened with these specific polymer compositions were found to form large size droplets in the aqueous-based, personal wash skin cleanser compositions of the invention. Again, large size droplets are greatly advantageous for deposition and delivery of the oil to the substrate (e.g., skin) from a personal skin cleansing product.

BACKGROUND OF THE INVENTION

Personal cleansing products which can deliver skin benefit to the skin (e.g., moisturization) are highly desirable. This is generally accomplished by ensuring that a sufficient amount of effective skin benefit agent is deposited on the skin during the skin cleaning process.

One particularly desirable group of skin benefit agents are the low viscosity (less than 1000 centipoise), hydrophobic emollient oils, such us sunflower oil and mineral oil (see Table 1 herein). These oils are substantive to the skin and are generally used as moisturizers. Higher viscosity oils are also beneficial, but if one is limited to use of only higher viscosity oils, the advantages of a vast array of skin benefit agents is simply lost.

Although many lower viscosity emollient oils (i.e. see Table 1) can be added to skin in "leave-on" type products (e.g., skin cream, moisturizer and lotion), they cannot be applied readily as aqueous-based skin cleansing compositions (e.g., surfactant containing personal wash compositions, such as shower gel and body wash liquid) because the non-thickened, low viscosity oils cause antifoaming (foaming is a strongly desired consumer attribute in cleansing compositions). Further, the non-thickened, low viscosity oils tend to present as small size droplets which do not readily deposit onto the skin and "deliver" the benefit agent. Finally, the low viscosity oil can readily cause phase separation from the bulk of the skin cleanser.

To overcome the disadvantages of the non-thickened low viscosity oils (antifoaming, small droplets, and phase separation), one can attempt to thicken them before adding them to a skin cleansing formulation. However, most of the thickeners used for this purpose (e.g., polyethylene waxes and aluminum stearate) are themselves highly antifoaming.

It is, therefore, a tremendous challenge to find a way of thickening low viscosity hydrophobic emollient oils in personal wash compositions without sacrificing foam/lather performance or colloidal stability. A thickener which does not antifoam or destabilize would also promote the formation of larger oil droplets which could be more readily deposited/delivered to the skin during a skin cleansing process.

Techniques of delivering hydrophobic skin benefit agents from personal cleansing formulations to the skin are reported in the prior art.

World patent applications WO 94/03152 and WO 94/03151 (assigned to Unilever NV and Unilever PLC), for example, teach the use of cationic hydrophilic polymers such as polymer JR® from Amerchol or Jaguar® from Rhone Poulenc to enhance the delivery of hydrophobic skin benefit agents (e.g., silicone, vegetable oils) onto the skin. These hydrophilic delivery polymers, however, may be dissolved in water and thus dissociate from the hydrophobic emollient oils in an aqueous-based formulation. In contrast, the hydrophobic polymeric thickeners used by the subject invention do not dissociate from the hydrophobic emollient oils.

World patent applications WO 94/01084 and WO 94/01085 (assigned to Proctor & Gamble Co.) teach a stable and mild soap personal cleansing and moisturizing composition that can deliver hydrophobic skin benefit agents on the skin. In order to deliver efficient deposition, however, these patent applications show that the droplet size of the skin benefit agents in the cleansers has to be large (i.e., the petrolatum used has particle size between 45 and 120 micrometers and viscosity between 60,000 to 400,000 cps). In contrast to the criticality of the subject invention, the referred patent applications do not teach or suggest thickening low viscosity hydrophobic oils (i.e., viscosity below 1000 cp) in a skin cleansing formulation to enhance skin benefits while at the same time avoiding significant antifoaming.

World patent applications WO 95/26710, WO 96/17591, WO 96/17592, and WO 96/25144 (assigned to Proctor & Gamble Co.) teach the delivery of hydrophobic lipid ingredients from personal cleansing bars and liquids to provide skin moisturizing benefit. The lipid ingredients (5 to 40% total composition) broadly claimed are hydrophobic materials selected from (a)hydrocarbons and waxes, (b) silicones and (c) different types of esters and have a viscosity in the range of 1000 to 500,000 cp. The referred patent applications, alone or in combination, do not teach or suggest the art of thickening low viscosity hydrophobic oils (i.e., viscosity below 1000 cp) in a skin cleansing formulation to enhance the skin benefits without sacrificing the lather performance. Also, the referred applications (i.e., WO 95/26710, Page 6, Line 5–7 and WO 96/25144, Page 14, Line 21–27) do not recognize the importance of using non-crystalline lipids to reduce the antifoaming effect; in which case, paraffins and other crystalline waxes (which all act effectively as antifoamers if used together with low viscosity emollient oils) are suggested in the same category with microcrystalline waxes and petrolatum (which cause much less antifoaming if combined with low viscosity oils). In contrast, the subject invention teaches the art how to formulate low viscosity emollient oils (viscosity below 1000 cp) thickened by a specific group of hydrophobic, oil-miscible polymers with a low degree of crystallinity in personal washing formulations. It further teaches enhancing the delivery of the low viscosity oils to the skin without sacrificing the lather performance. In the subject invention, crystalline waxes such as paraffins and polyethylene are specifically excluded from the oil thickeners used.

World patent application WO 94/17166 teaches a cleansing composition comprising insoluble nonionic oil or wax or mixture of oil and/or wax (3 to 40% total composition) for providing a skin benefit from the claimed cleanser composition. Applicants have found that wax in oils function as an antifoaming agent and use of such waxes as thickening agents is specifically disclaimed by the subject invention. Also, in contrast to the criticality of the subject invention, the referred patent application does not teach or suggest thickening low viscosity hydrophobic oils (i.e., viscosity below 1000 cp) in a skin cleansing formulation to enhance the skin benefits without antifoaming.

World patent application WO 92/08444 (assigned to Proctor & Gamble Co.) teaches a mild cleansing bar composition comprising 0.5 to 20% of a hydrophobic silicone component consisting of (A) silicone gum (viscosity greater than 600,000) and (B) silicone fluid with a viscosity between 5 to 600,000. The referred solid bar application is fundamentally different from the subject liquid application in terms of processing and composition. Further, the referred patent application only teaches the mixing of one specific type of hydrophobic emollients (i.e., polydimethylsiloxanes of low viscosity, (B)) with the same type of emollient oils of higher viscosity (i.e., PDMS, (A)) to promote desired skin feel and mildness. In contrast, in order to achieve synergistic skin benefits, the subject invention teaches the art how to thicken a broad range of low viscosity (less than 1000 cp) oils using specific polymer thickeners which are structurally completely different than the PDMS, or how to thicken a broad range of low viscosity, non-silicone oils using hydrophobic, high viscosity silicone oil. As such, low viscosity oils and thickeners which have a completely different structure than the low viscosity oils together provide synergistic benefits to the skin, and as such, the mixture of low viscosity and high viscosity silicones claimed by the referred application is clearly different than the thickened oils claimed by the subject invention.

The use of oils which act as benefit agents and polymers of the invention which are thickeners is also known.

U.S. Pat. No. 5,221,534 to P. DesLauriers (Pennzoil Products Company), for example, teaches health and beauty aid compositions contained in a gel comprising a mineral oil and blends of di- and tri-block copolymers based on synthetic thermoplastic rubbers. The patent teaches how to make gels that may also include other moisturizing agents. However, this patent and other literature published by Penreco (a division of Pennzoil) only teach applications of the gels in "leave-on" type products, such as body moisturizer and lotion which do not contain the lathering surfactants used by this invention, and fails to teach or suggest the inclusion of the gels in any personal washing formulations containing lathering surfactants.

By contrast, the subject invention is distinct in at least two important ways. First, the subject invention uses the polymer thickened oils and/or the oil/polymer blend itself as a thickener for other (same or different) low viscosity oils. Second, those oil/polymer compositions are used in personal wash compositions, not leave-on type products.

Different from leave-on type formulations (i.e., the one claimed by US. Pat. No. 5,221,534 which contains no lather surfactant), the personal washing formulations claimed by the subjective invention comprises at least 5% wt., preferably 10% wt. or greater the lathering surfactants. Further, the compositions of the invention will generate foam height of at least seven cm or greater after two minutes of foam aging by the Ross-Miles method (see Methodology in the Example sec.). Such foam heights would not be generated by "leave-on" products.

Soap/cosmetics/Chemical Specialties (Page 24, February, 1996) reported a Shower-Active™ moisturizer introduced by Jergens in November, 1995. The moisturizer contains the mineral oil/polymer gels (Geahlene®) claimed by U.S. Pat. No. 5,221,534 and other ingredients, such as octyl isononanoate, steareth-2, and phosphoric acid. The moisturizer can be applied to skin in the shower to avoid the time-consuming process of applying the moisturizer after the shower. Again, however, this reference discloses the oil/polymer gels by themselves in leave-on compositions, such as body moisturizer, cream and lotion. The reference does not disclose the oil/polymer gel composition as thickeners for additional low viscosity oil (i.e., to help deposit without antifoaming) and further does not disclose the use of these polymer thickened oil compositions in personal wash compositions. Again, said "leave-on" type products comprising Geahlene® do not contain the lathering surfactants used by the subjective invention to promote the lather, which is an important desired sensory cue for personal washing products.

As described in the prior art, a wide variety of hydrophobic emollient oils are desirable skin benefit agents. However, because they are antifoaming, potentially destabilizing, and do not readily deposit, low viscosity (less than 1000 cp) hydrophobic emollient agents as moisturizers are difficult to be included in personal washing formulations. Examples of such low viscosity oils include mineral oils, sunscreen oils, vegetable oils, low molecular weight lactate esters and isopropyl myristate.

While not wishing to be bound by theory, applicants believe that these low viscosity oils are emulsified easily by surfactants and thus (1) cause antifoaming and (2) are difficult to be effectively retained onto the skin during a skin cleansing (washing) process. In contrast, high viscosity oils (i.e., viscosity significantly greater than 1000 cp) are less emulsifiable and therefore form larger droplets in a cleanser, and this is desired for high foaming and oil deposition onto the skin. However, focusing on only such high viscosity oils would leave a vast array of low viscosity oils which are potentially wonderful moisturizers, but simply could not previously be effectively used.

One route for effectively depositing low viscosity oils onto the skin from a cleanser is to thicken the oils using thickening agents. It was found, however, that most conventional oil thickeners, such as paraffin wax, crystalline polyethylene, silica, fumed silica, silicate, and long chain (i.e., $C_{18}$–$C_{22}$) fatty acid soap, all have a strong tendency to significantly depress the lather of a cleanser, especially in the presence of hydrophobic emollient oils. That is, personal wash cleanser compositions containing those thickened oils can deliver skin moisturizing benefits but fail to provide satisfactory lather performance.

In short, the prior art teaches one of two situations:
(1) personal wash compositions where low viscosity oils are thickened by known thickeners, but foaming (and/or stability) is compromised; or
(2) low viscosity oils which are thickened by specific polymers (e.g., like the Pennzoil Geahlene® composition), wherein these polymer thickened oils are used in leave-on compositions for delivering the oil as a moisturizer.

Novel to the art, the subject invention formulated low viscosity emollient agents pre-thickened by a group of specific hydrophobic, non-antifoaming polymers into skin cleansing formulations, and the invention provides at least three unique benefits in comparison to non-thickened low viscosity oils. First, the specific polymer thickened oils provide significantly better lather performance. Second, the thickened oils tend to form larger size droplets more adhesive to the skin, which may in turn enhance the oil deposition onto skin (supported by the prior art listed above, i.e., World patent applications WO 94/01084 and WO 94/01085). Third, the specific polymer thickened oils tend to be stable in a properly-designed skin cleanser formulation and resist phase separation from the bulk body of the formulation.

BRIEF SUMMARY OF THE INVENTION

Surprisingly and unexpectedly, applicants have found that it is possible to effectively thicken hydrophobic low viscosity emollient oils (viscosity less than 1000 cp) using a special group of hydrophobic polymeric thickeners such that the low viscosity oils can be more effectively delivered from personal wash cleanser compositions without compromising foaming. That is, it is now possible to deliver cleansing (through surfactants), moisturization (through low viscosity oil thickened by the specific polymer compositions) and good foaming all in one composition.

More specifically, the present composition comprises an aqueous-based personal wash cleanser composition comprising:

(a) 5% to 50%, preferably 10–30% by wt. of a lather surfactant selected from the group consisting of anionic surfactants, cationic surfactants, amphoteric surfactants, nonionic surfactants and mixtures thereof, (b) 0.5% to 30%, preferably 5% to 25% by wt. total composition a pre-thickened oil composition having a viscosity above 2000 cp, preferably above 5000 cp, and most preferably above 10,000 cp at 25° C., wherein the pre-thickened oil composition comprises a hydrophobic emollient agent with viscosity less than 1000 cp and a thickening material that is specified in the detailed embodiment of this invention.

DETAILED DESCRIPTION OF THE INVENTION

The present invention relates to novel aqueous based personal wash cleanser compositions which are not only able to deliver cleansing benefits normally associated with such cleansers, but are also able to deliver much higher amounts of low viscosity oil (e.g., much greater moisturization benefits) than previously possible without compromising foam attributes. Stated differently, when low viscosity oil is normally thickened (as is required to provide moisturization benefits), the thickeners which have been previously used in the art (e.g., wax) have also compromised foaming in the cleanser composition.

While low viscosity oil (i.e., mineral oil with a viscosity around 12 cp at 20° C.) has been thickened in the prior art using one of the specific polymer thickening agents selected by the subject invention (i.e, component (b)(ii), Geahlene® type compositions), the oil/polymer compositions have never previously been used in skin cleanser compositions.

Unexpectedly, however, applicants have now found that low viscosity (less than 1000 cp) oils thickened with specific polymer compositions (e.g., Geahlene® type compositions) can be used in cleanser compositions and permit the cleanser compositions to function as normal cleansers while providing moisturization function and without simultaneously compromising foaming. As such, the compositions of the invention contain at least 5% wt. or greater the lather surfactant (see Detailed Description, (a) Surfactant System) and will generate foam height of at least seven cm or greater after two minutes of foam aging by the Ross-Miles method (see Methodology in the Example sec.). This ability of foam generation differentiates the claimed skin cleansing composition from those "leave-on" type skin care products, such as moisturizer, cream and lotion. In contrast, an aqueous cleanser containing the same percentage of the same low viscosity oil (viscosity less than 1000 cp) which has been pre-thickened by crystalline thickeners, such as polyethylene or paraffin waxes, $C_{18}$–$C_{22}$ water insoluble fatty acid soap, usually provides significantly less lather (see Example section).

Thus, applicants have remarkably been able to obtain a desirable dual benefit (moisturizer from the low viscosity oil and improved foam) in a cleanser composition, an achievement not previously obtained in the art using low viscosity oils. Instead, the oil has previously been forced to disregard a whole category of oils/benefit agents because there has previously been no suitable way to incorporate a significant amount of them (i.e., 20% wt.) into personal wash compositions.

The composition of the invention comprises:

(a) 5% to 50%, preferably 10–30% by wt. of a surfactant selected from the group consisting of anionic surfactants, cationic surfactants, amphoteric surfactants, nonionic surfactants and mixtures thereof;

(b) 0.5% to 30%, preferably 5% to 25% by wt. total composition a specific 'non-antifoaming' polymer thickened oil composition with a viscosity above 2000 cp, preferably above 10,000 cp;

wherein the pre-thickened oil composition (b) comprises a hydrophobic emollient agent with viscosity less than 1000 cp and a "non-antifoaming" thickening material that is specified further below;

wherein by "non-antifoaming" is meant that the said cleanser containing the polymer/oil thickening composition generate foam height of at least seven cm or greater after two minutes of foam aging, as tested by the Ross-Miles or the Cylinder-shaking methods detailed in Methodology). In contrast, a cleanser containing the same percentage of the same low viscosity oil (viscosity less than 1000 cp) thickened by crystalline thickeners, such as polyethylene or paraffin waxes or $C_{18}$–$C_{22}$ fatty acid soap, usually generates significantly less lather (see Example section).

Each component is further detailed below:

(a) Surfactant System

Anionic Surfactants

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, C8–C22 hydroxyalkane sulfonate or alkyl glyceryl ether sulfonate (AGS); or an aromatic sulfonate such as alkyl benzene sulfonate.

The anionic surfactant may also be a salt of $C_8$–$C_{22}$ carboxylic acid (or known as fatty acid soap). The fatty acid soap is also known to be more irritative to skin than other mild anionic surfactants, such as sodium cocoyl isethionate. As such, the skin cleansing formulations claimed by this invention comprise less than 10% said salt of carboxylic acid.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$RO(CH_2CH_2O)_nSO_3M$ wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation;
amido-MIPA sulfosuccinates of formula $$RCONH(CH_2)CH(CH_3)(SO_3M)CO_2M$$

where M is as defined above.

Also included are the alkoxylated citrate sulfosuccinates; and
alkoxylated sulfosuccinates such as the following:

$$R-O-(CH_2CH_2O)_n\overset{O}{\overset{\|}{C}}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula $R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R-(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

$$\overset{O}{\overset{\|}{R}C}-O-\overset{X}{\overset{|}{C}H}-CH_2-(O\overset{Y}{\overset{|}{C}H}-CH_2)_m-SO_3^-M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

In general the anionic component will comprise from about 1 to 20% by weight of the composition, preferably 2 to 15%, most preferably 5 to 12% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

$$R^2-Y^{(+)}\overset{(R^3)_x}{\overset{|}{-}}CH_2-R^4Z^{(-)}$$

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatetradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl) ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

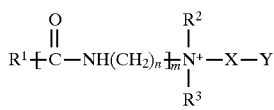

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is —$CO_2$— or —$SO_3$—

Suitable amphoteric detergents within the above general formula include simple betaines of formula:

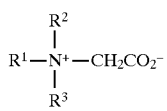

and amido betaines of formula:

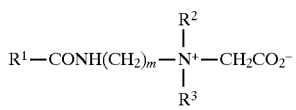

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

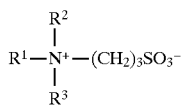

or

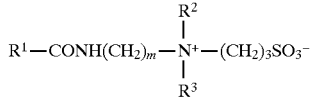

where m is 2 or 3, or variants of these in which —$(CH_2)_3$ $SO^-_3$ is replaced by

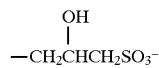

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 5% to 15% of the composition.

In addition to one or more anionic and optional amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$–$C_{22}$) phenols-ethylene oxide condensates, the condensation products of aliphatic ($C_8$–$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula

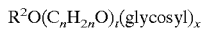

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

The nonionic surfactant can also be a water soluble polymer chemically modified with hydrophobic moiety or moieties. For example, EO-PO block copolymer, hydrophobically modified PEG such as POE(200)-glyceryl-stearate can be included in the formulations claimed by the subject invention.

(b) Oil/Polymer Thickening Compositions

Examples (not intended to be limiting in any way) of the type of hydrophobic emollient oils (b)(i) contemplated by this invention include as follows:

TABLE 1

Viscosity of Some Hydrophobic Emollient Oils

| Material Names | Temperatures (degree C.) Significant to Skin Cleansing | Viscosity (Centipoise) |
| --- | --- | --- |
| Sun Flower Seed Oil | 20 | 10 |
| Mineral Oil | 20 | 12 |
| Olive Oil | 40 | 36 |
| Caster Oil | 30 | 451 |
| Oleic Acid | 30 | 26 |
| Rthe ape Oil | 30 | 96 |
| Soybean Oil | 30 | 41 |

To thicken a low viscosity hydrophobic oil and make the thickened oil stable in an aqueous skin cleanser without sacrificing lather performance, the polymeric thickeners (b)(i) used in this invention must meet the all the following criteria at a temperature between 10° C. and 60° C.

(1) hydrophobicity:

a polymer or a blend of polymers that have a water solubility less than 1% by wt. in water, preferably less than 0.5% by wt. in water.

The hydrophobicity is critical because the thickening agent has to be stable in the oil in the aqueous cleansing formulation;

(2) low crystallinity:

a polymer or a blend of polymers which contain 80% wt or greater non-crystalline polymeric materials and less than 20% crystalline polymeric materials in a continuous matrix of the oil that it thickens.

In the subject invention, the non-crystalline polymeric materials comprise gels, amorphous solids, microcrystalline waxes and mixtures thereof. Gels and amorphous solids can be distinguished from crystalline materials by the wide-angle X-ray diffraction technique (crystalline materials provide distinct X-ray diffraction maxima, and gels and amorphous solids do not).

Microcrystalline wax is a special case. Unlike those crystalline waxes (i.e., paraffins and polyethylene), microcrystalline waxes (historically known as amorphous waxes) are of higher molecular weight, highly branched hydrocarbon chains, smaller crystalline or amorphous structure (depending on the processing routes used), and much higher oil compatibility and plasticity (see: H. Bennet, Industrial Waxes, Page 89–92, published by Chemical Publishing Company, 1963, hereby included by reference into the subject application). Those unique properties and the differences between microcrystalline waxes and crystalline waxes are summarized in Table 2.

The most popular product of microcrystalline waxes is petrolatum (also known as petroleum jelly or mineral jelly), which consists of about 90% wt. a natural mixture of microcrystalline waxes plus minor amount of other impurities. Other examples of microcrystalline waxes include but are not limited to Micro. Wax, Micro. Wax 2305, Micro. Wax 1135/15W (all from Ross), and Multiwax 180M, Multiwax ML-445, Multiwax 180W, Multiwax W-445, Multiwax W-445, Multiwax W-835, Multiwax X-145 (all from Witco/Sonneborn).

TABLE 2

Major differences between microcrystalline waxes and crystalline waxes

| Major Differences | Crystalline waxes | Microcrystalline waxes |
| --- | --- | --- |
| Manufacturing process | by pressing a paraffin wax distillate and sweating the resulting slack wax for the final oil removal. | By further solvent crystalization from the wax distillate residua. |
| Molecular Morphology | mainly straight hydrocarbons | mainly highly branched hydrocarbons |
| Molecular Weight | lower MW (i.e., 360–420). | higher MW (i.e, 580–700). |
| Crystalline Structure | large, well formed crystals (i.e., >100 microns) from wax melt or solvent. | small, irregular crystals (i.e.,<5 microns) from wax melt, but amorphous materials from solvent. |
| Mechanical Properties | hard and brittle at solid state and shatter under compression, low viscosity fluid at molten state | plastic and flow under compression at gel state, viscous liquid at molten state |
| Oil Compatibility | little affinity for oil | dispersable with many oils that leads to enhanced homogenous plastic mix |
| Appearance as a Film | transparent | opalescent (white, brown or black in color) |
| Thermal Contraction Coefficient (from liquid to solid or gel state) | greater | much less |

Low crystallinity is critical because a high order of crystallinity (i.e., paraffin or polyethylene waxes) in the thickened oil causes significant antifoaming;

(3) oil compatibility:

a polymer or a blend of polymers which are miscible and/or dispersible in a low viscosity oil (viscosity less than 1000 cp) to form a homogenous mix that is stable in the subject liquid cleanser formulation without composition and layer separation. Oil compatibility is critical because the polymer thickener and the oil have to form a homogenous domain (i.e, thickened oil droplets) in the aqueous-based skin cleansing formulation.

Examples of the potential polymer thickeners that meet the above criteria include but are not limited to:

(1) rubber-based thermoplastic block copolymer, such as SEBS, SEP, SEB, EP, SBS, and SIS, in which E=polyethylene segments, S=polystyrene segments, B=polybutylene or polybutadiene segments, l=polyisoprene segments, P=polypropylene segments.

These copolymers are commercially available from Shell Chemical Company (under the tradename of Kraton®);

(2) silicone oil with a viscosity higher than 2000 cp, preferably higher than 5000 cp, and most preferably higher than 10,000 cp, selected from high molecular weight polydimethylsiloxanes, and other hydrophobic polydimethylsiloxane derivatives such as diethylpolysiloxane, dimethicone, C1–C30 alkyl polysiloxane. Those silicone oils are commercially available. For example, polydimethylsiloxanes of different molecular weight and viscosity are commercially available from Dow Corning under the trade name of Dow Corning 200 fluid or from General Electric under the trade name of GE silicone; and (3) Microcrystalline waxes with a viscosity higher than 2000 cp, preferably higher than 5000 cp, and most preferably higher than 10,000 cp, such as petrolatum, which is available from Ultra Chemical Inc. (tradename as Ultrapure SC or Ultrapure HMP white petrolatum) or from Fisher Scientific (Petrolatum, Purified Grade); such as Micro. Wax, Micro. Wax 2305, Micro. Wax 1135/15W (all from Ross), and such as Multiwax 180M, Multiwax ML-445, Multiwax 180W, Multiwax W-445, Multiwax W-445, Multiwax W-835, Multiwax X-145 (all from Witco/Sonneborn).

While not wishing to be bound by theory, applicants of the subject invention believe that the polymeric thickeners form a network type structure that microscopically disperses in the low viscosity oil, and that a polymeric network is formed through physical entanglement (i.e., PDMS or petrolatum in IPM or sun flower seed oil, see Type 2 and type 3 below) or micro-domain aggregation (i.e., rubber-based block copolymers in mineral oil, Type I below).

Examples of detailed polymer/oil thickening compositions are specified below.

Type 1 Copolymer Thickened Mineral Oil (i.e., Commercially Available Geahlene®)

A low viscosity emollient oil thickened by a specific group of rubberbased thermoplastic block copolymers meets the above criteria. The oil/block copolymer thickening composition is claimed by U.S. Pat. No. 5,221,534 to DesLauriers et al. Under this patent, the oil/copolymer thickening compositions are currently sold/marketed under the trademark of Geahlene® by Penreco as "leave on" type skin care products, such as health and beauty aid products, which contain no lathering surfactants as used by the subject invention to promote lather.

The polymer surrounding the oil in this thickening composition is a blend of polymers used comprising at least two polymers or copolymers selected from the group consisting of diblock polymers which contain at least two thermodynamically incompatible segments, triblock copolymers, radial polymers or copolymers, multiblock polymers or copolymers, and mixtures thereof, it being required however, that at least one diblock copolymer and/or triblock copolymer be present in the composition.

The at least one diblock copolymer or said at least one triblock copolymer comprises 5% to 95% of said blend of at least two different polymers, and said diblock and triblock polymers comprise segments of styrene monomer units and rubber monomer units.

Preferably the blend is a mixture of diblock copolymers and triblock copolymers. By the expression thermodynamically incompatible with respect to the polymers is meant that the polymer contains at least two incompatible segments, for example at least one hard and one soft segment. In general in the diblock polymer, segments will be sequential with respect to hard and soft segments. In a triblock polymer, the ratio is two hard, one soft, two hard, one soft, etc. or a 2-1-2 copolymer. The multiblock polymers can contain any combination of hard and soft segments. As noted above, in the composition, however, there must always be present at least one of the diblock or triblock copolymers. There must also be a combination which will provide both the hard and soft characteristics necessary for the composition. These characteristics are necessary in order to provide the controlled syneresis which is an essential part of the present invention in formation of the health and beauty aid gel compositions.

In the compositions, the oil is contained within the polymer network formed by the polymer blend.

The polymers and the oil/polymers complex are described more specifically in U.S. Pat. No. 5,221,534 to DesLauriers et al., which patent is hereby incorporated by reference in the subject application.

Type 2 Silicone Oil Thickened Emollient Oils

In another embodiment of the invention, a low viscosity, non-silicone emollient oil (viscosity less than 1000 cp) thickened by high-viscosity silicone oil, such as polydimethylsiloxane (PDMS) also meet the above criteria that define the polymer thickeners selected.

The viscosity of PDMS is above 2000 cp, preferably above 5000 cp, and most preferably above 10,000 cp.

The PDMS I oil thickening system comprises 10% to 90% by wt. said PDMS, and 90% to 10% by wt. silicone soluble low viscosity emollient oils that include but are not limited to the following:

diisopropyl adipate, diisopropyl sebacate, octyl isononanoate, isodecyl octanoate, diethylene glycol, isopropyl myristate, isocetyl palmitate, isopropyl isostearate, isocetyl palmitate, isostearyl palmitate, diisostearyl malate, diglyceryl isostearate, diisopropyl dimerate, diglyceryl diisostearate, and mixtures thereof.

The PDMS/oil thickening system can also comprises 20% to 95% said PDMS, and 5% to 80% by wt. low viscosity oils that are homogeneously dispersible and/or partially soluble in PDMS, which include but are not limited to:

mineral oil, lanolin oil, coconut oil, jojoba oil, maleated soybean oil, almond oil, peanut oil, wheat germ oil, rice bran oil, linseed oil, apricot pits oil, walnuts, palm nuts, pistachio nuts, sesame seeds, rape seed oil, cade oil, corn oil, peach pit oil, poppyseed oil, pine oil, soybean oil, avocado oil, sunflower seed oil, hazelnut oil, olive oil, grapeseed oil, and safflower oil, babassu oil, and mixtures thereof.

Type 3 Microcrystalline Waxes (e.g., Petrolatum) Thickened Emollient Oils

In another embodiment of the invention, microcrystalline waxes with a viscosity higher than 2000 cp, preferably higher than 5,000 cp, and most preferably higher than 10,000 cp, can also be used to thicken low viscosity emollient oils. An example of this type of thickener is petrolatum that is dominantly a natural mixture of microcrystalline waxes; an example of petrolatum is a Petrolatum from Fisher Chemical (purified grade).

The gel/oil thickening composition comprises 10% to 80% by wt. said microcrystalline waxes and 20% to 90% by wt. low viscosity hydrophobic emollient oils that can be finely dispersed and/or dissolved in the hydrocarbon gel. The oils include but are not limited to:

mineral oil, lanolin oil, coconut oil, jojoba oil, maleated soybean oil, almond oil, peanut oil, wheat germ oil, rice bran oil, linseed oil, apricot pits oil, walnuts oil, palm nuts oil, pistachio nuts oil, sesame seeds oil, rape seed oil, cade oil, corn oil, peach pit oil, poppyseed oil, pine oil, soybean oil, avocado oil, sunflower seed oil, hazelnut oil, olive oil, grapeseed oil, and safflower oil, Shea butter, babassu oil, isopropyl myristate and mixtures thereof.

As noted above, it is the specific polymeric thickening agents which allow the low viscosity oil to deliver improved moisturization effect while providing significantly less antifoaming in comparison to the non-thickened oil or oil thickened by crystalline waxes (i.e., paraffins and polyethylene) and $C_{18}$–$C_{22}$ fatty acid soap. As an additional advantage, the polymer/oil thickening compositions are stable in the claimed liquid skin cleansing formulations and resist phase separation.

(c) Other Optional Ingredients

In addition, the compositions of the invention may include optional ingredients as follows:

Organic solvents, such as ethanol; auxiliary thickeners, such as carboxymethylcellulose, magnesium aluminum silicate, hydroxyethylcellulose, methylcellulose, carbopols, glucamides, or Antil® from Rhone Poulenc; perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4' trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used include Quatrisoft LM-200 Polyquaternium-24, Merquat Plus 3330-Polyquaternium 39; and Jaguar® type conditioners.

Polyethylene glycols which may be used include:

| Polyox | WSR-205 | PEG 14M, |
|--------|---------|----------|
| Polyox | WSR-N-60K | PEG 45M, or |
| Polyox | WSR-N-750 | PEG 7M. |

PEG with molecular weight ranging from 300 to 10,000 Dalton, such as those marketed under the tradename of CARBOWAX SENTRY by Union Carbide.

Thickeners which may be used include Amerchol Polymer HM 1500® (Nonoxynyl Hydroethyl Cellulose); Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another optional ingredient which may be added are the deflocculating polymers such as are taught in U.S. Pat. No. 5,147,576 to Montague, hereby incorporated by reference.

Another ingredient which may be included are exfoliants such as polyoxyethylene beads, walnut shells and apricot seeds The compositions may also contain 0.1 to 15% by wt., preferably 1 to 10% by wt. of a structurant. Such structurants can be used to avoid addition of external structurants (e.g., cross linked polyacylates and clays) if suspending particles is desired as well as to provide desirable consumer attributes.

The structurant is generally an unsaturated and/or branched long chain ($C_8$–$C_{24}$) liquid fatty acid or ester derivative thereof; and/or unsaturated and/or branched long chain liquid alcohol or ether derivatives thereof. It may also be a short chain saturated fatty acid such as capric acid or caprylic acid. While not wishing to be bound by theory, it is believed that the unsaturated part of the fatty acid of alcohol or the branched part of the fatty acid or alcohol acts to "disorder" the surfactant hydrophobic chains and induce formation of lamellar phase.

Examples of liquid fatty acids which may be used are oleic acid, isostearic acid, linoleic acid, linolenic acid, ricinoleic acid, elaidic acid, arichidonic acid, myristoleic acid and palmitoleic acid. Ester derivatives include propylene glycol isostearate, propylene glycol oleate, glyceryl isostearate, glyceryl oleate and polyglyceryl diisostearate.

Examples of alcohols include oleyl alcohol and isostearyl alcohol. Examples of ether derivatives include isosteareth or oleth carboxylic acid; or isosteareth or oleth alcohol.

The structuring agent may be defined as having melting point below about 25° C. centigrade.

The present invention is set forth in greater detail in the examples which follow. The examples are for illustration purposes only and are not intended to limit the scope of the claims in any way.

All percentages in the examples and specification, unless indicated otherwise, are intended to be percentages by weight.

EXAMPLES

Methodology of Lather Assessments

Ross-Miles Method

Foam height was measured by the Ross-Miles method (for detail, see J. Ross and G. D. Miles, Am. Soc. for Testing Materials, Method D1173-53, Philadelphia, Pa., 1953). In this invention, 200 ml of a test solution comprised of 0.5% by wt. total surfactant concentration contained in a pipette of specified dimensions with a 2.9 mm I.D. orifice are allowed to fall 90 cm onto 50 ml of the same solution contained in a cylindrical vessel maintained at a given temperature (40° C.) by means of a water jacket. The height of the foam produced in the cylindrical vessel is read immediately after all the solution has run out of the pipette ("initial foam height") and then again after given amount of time (foam aging time).

Cylinder-Shaking Method

Foam volume was also tested using a cylinder-shaking method. Forty grams of solution (2.5% by wt. total surfactant concentration) was put in a 250 ml PYREX cylinder with cap. Foam was generated by shaking the cylinder (by a trained evaluator) for 0.5 minute. After the foam settled for 2.5 minutes, the foam height was measured.

Hand-Washing Method

A hand-wash lather test method was used to measure the lather volume produced by different types of thickened oils. The procedure of the test method is described below:

1. Wet both gloved (latex glove) hands with warm tap water;
2. 0.7 grams of cleanser and 1.0 grams water were applied on the wet right palm;
3. Wet left palm was rubbed back and forth 20 times on right palm to generate lather;
4. lather was collected from both palms into a graduated beaker;
5. The above procedure was repeated two more times and the generated lather was collected in the same beaker. The total lather volume collected in the beaker was measured and summarized in Table 1 (Example 3).

Example 1

Preparation of Thickened Oils

The lather performance of a cleanser containing the polymer/oil thickening compositions preferred by the subject invention was compared to that of a cleanser containing oils thickened by non-preferred agents. For this purpose, oils thickened by different materials were prepared for the lather testing that is demonstrated in the following examples.

Geahlene® Polymer Thickened Oils (A Preferred Example of the Invention)

The commercially available Geahlene® 1600 (from Penreco), a mineral oil thickened by a specific blend of rubber-based thermoplastic polymers (a preferred example of this invention), was directly applied without further modification.

Wax or Silica Thickened Oils (Non-preferred, Comparative)

The other two oils thickened either with crystalline polymer (wax) or hydrophobic particle (silica) are non-preferred thickened oils. One was prepared by mixing 90 parts of the mineral oil (Drakeol 7 ex Penreco) and 10 parts of crystallized polyethylene (Polywax 2000 ex. Petrolite Specialty Polymer Group) at 70° C. using a overhead mixer to form a clear solution first. Then the solution was cooled to room temperature to form a viscous gel. The other was prepared by mixing 10 parts of hydrophobic particles (Cab-O-Sil TS720 fumed silica ex Cabot Corporation) with 90 parts of mineral oil at room temperature for 30 minutes. A semi pasty thickened oil was formed after mixing the hydrophobic particles into the mineral oil.

Example 2
Preparation of Personal-Washing Cleansers Containing the Oils Thickened by Different Thickeners A liquid cleanser with compositions shown in Formulation 1 was used to prepare Formulation No. 2 to No. 5 (in Example 3). Formulations No. 2, 3 and 4 were prepared by mixing 5% by wt. of the three different kinds of thickened oils respectively with 95% wt. of Formulation No. 1 at 10 RPM for 5 minutes using a overhead mechanical mixer. Formulation No. 5 was prepared by mixing 10 wt. % of the commercial Geahlene® 1600 directly with 90 wt. % of Formulation 1 at the same mixing condition.

Formulation No. 1 (Skin Cleanser Base)

| Composition | % wt. |
| --- | --- |
| Cocoamidopropyl Betaine | 10.0% |
| Sodium cocoyl Isethionate | 5.0% |
| Sodium Laureth Sulfate | 5.0% |
| Propylene Glycol | 2.0% |
| Clay | 0.6% |
| Glydant Plus (ex Lonza) (a bacteriostat) | 0.2% |
| Antil 141 (ex Goldschmidt) (thickener, CTFA adopted name: propylene glycol (and) PEG-55 propylene glycol oleate) | 0.6% |
| Perfume | 1.0% |
| water | up to 100% by wt. |

Formulation No. 2 (Invention, Cleanser+5% Geahlene)
 95 wt. % liquid cleanser of Formulation No. 1;
 5 wt. % Geahlene® 1600.
Formulation No. 3 (Comparative, Cleanser+5% wax thickened oil)
 95 wt. % liquid cleanser of Formulation No. 1;
 5 wt. % polyethylene (Polywax 2000) thickened oil.
Formulation No. 4 (Comparative, Cleanser+5% silica thickened oil)
 95 wt. % liquid cleanser of Formulation No. 1;
 5 wt. % hydrophobic particle (Cab-O-Sil TS720 fumed silica) thickened oils.

Formulation No. 5 (Invention, Cleanser+10% Geahlene)
 90 wt. % liquid cleanser of Formulation No. 1;
 10 wt. % non-crystallized polymer (Geahlene 1600) thickened oil.

Example 3
Effect of Oil Thickeners on Cleanser's Lather

By using the hand-washing method, the lather volume produced by cleansers containing different types of thickened oils was measure, and the results are shown in Table 3.

TABLE 3

Lather Volume of Example 2-5 in Comparison to that of Control

| Composition | Lather Volume |
| --- | --- |
| Formulation 1 (Control) | 60 ml |
| Formulation 2 (Invention) | 55 ml |
| Formulation 3 (Comparative) | 25 ml |
| Formulation 4 (Comparative) | <5 ml |
| Formulation 5 (Invention) | 45 ml |

The data clearly indicate that the oils thickened by Geahlene® 1600 (Formulation No. 2 and Formulation No. 5) have less antifoaming effect on the cleanser than the oils thickened by crystalline PolyWax and fumed silica.

Example 4
Shower-gel Formulations Containing High Levels of Geahlene-thickened Oils Mineral oils thickened by rubber-based hydrophobic copolymers, such as Geahlene® gels (mineral oil/thermoplastic rubber copolymer mixture by Penreco) can also be included in a shower gel formulation at relatively high levels without sacrificing lather performance and product stability.

In this example, the base formulation used is shown in Formulation No. 6. The ingredients were blended at 40° C. for two hours using an overhead blender, then the mixture was cooled to room temperature. The resulting formulation was a creamy, homogenous, and pourable gel.

Formulation No. 6 (Skin Cleanser Base)

| Composition | % wt. |
| --- | --- |
| Cocoamidopropyl betaine (trade name: F40, from Goldschmidt) | 10.0% |
| Sodium laurylether (3EO) sulfate (trade name: CS-330, from Stepan) | 5.0% |
| Sodium cocoyl isethionate (Jordapon, from Rhone Poulenc) | 5.0% |
| Water | to 100% |

Using the same preparation method, 25% by wt. Geahlene® 750 (a mineral oil/non-crystalline polymer blend by Penreco) was mixed into the base formulation, as shown in Formulation No. 7.

Formulation No. 7 (Cleanser+25% Geahlene)

| Composition | % wt. |
| --- | --- |
| Cocoamidopropyl betaine (trade name: F40, from Goldschmidt) | 10.0% |
| Sodium laurylether (3EO) sulfate (trade name: CS-330, from Stepan) | 5.0% |
| Sodium cocoyl isethionate (Jordapon, from Rhone Poulenc) | 5.0% |

-continued

| Composition | % wt. |
| --- | --- |
| Geahlene ® 750 | 25.0% |
| Water | to 100% |

The foam heights by the Ross-Miles method (at T=40° C. and dilution factor=40x, total surfactant concentration= 0.5% by wt.) for Formulation No. 6 and No. 7 were measured respectively as a function of foam aging time. As shown in Table 4, Formulation No. 7 with Geahlene® 750 had the foam height and foam stability comparable to those of Formulation 6, which did not contain any hydrophobic oil.

TABLE 4

Ross-Miles Foam Heights for Formulations No.6 and No.7 as a Function of Foam Aging Time

| Foam Aging Time (minutes) | Foam Height (cm, standard deviation = +/− 2 cm) (Formulation No.6) | Foam Height (cm, standard deviation = +/− 2 cm) (Formulation No.7) |
| --- | --- | --- |
| 0.8 | 18 | 18 |
| 1.7 | 17 | 18 |
| 2.5 | 17 | 18 |
| 4.1 | 17 | 17 |
| 6.2 | 16 | 17 |
| 8.0 | 16 | 17 |
| 10 | 16 | 17 |

This example shows clearly that large amounts of the polymer/oil thickening composition (e.g., 25% Geahlene® 750) can provide therefore moisturization benefits without affecting the foam height whatsoever.

Example 5
Shower-gel Formulations Containing Isopropyl Myristate Thickened by Geahlene(R) 1600

Without sacrificing the lather performance of a skin cleanser, the commercial Geahlene® 1600 (from Penreco) can also thicken low viscosity oils other than the mineral oils. In this example, isopropyl myristate (IPM) was significantly thickened by Geahlene 1600 (from Penreco) at 1:1 weight ratio after mixed at 20° C. using a overhead mixer. Then the 20% wt. of this Geahlene-IPM thickening compositions was blended with the surfactant base of Formulation No. 6 using the same preparation method, which resulted in Formulation 8. The resulting formulation is a creamy, homogenous, and pourable gel.

Formulation No. 8 (Invention)

| Composition | % wt. |
| --- | --- |
| Cocoamidopropyl betaine (trade name: F40, from Goldschmidt) | 10.0% |
| Sodium laurylether (3EO) sulfate (trade name: CS-330, from Stepan) | 5.0% |
| Sodium cocoyl isethionate (Jordapon, from Rhone Poulenc) | 5.0% |
| Isopropylmyristate/Geahlene ® 1600 (1:1 wt. ratio) pre-thickened oil composition | 20.0% |
| Water | to 100% |

By the same preparation method as Formulation No. 6 to No. 8, 10% by wt. IPM was blended with the surfactant base of Formulation 6 for the purpose of comparison, and the resulted mixture is Formulation No. 9.

Formulation No. 9 (Comparative)

| Composition | % wt. |
| --- | --- |
| Cocoamidopropyl betaine (trade name: F40, from Goldschmidt) | 10.0% |
| Sodium laurylether (3EO) sulfate (trade name: CS-330, from Stepan) | 5.0% |
| Sodium cocoyl isethionate (Jordapon, from Rhone Poulenc) | 5.0% |
| Isopropylmyristate | 10% |
| Water | to 100% |

The Profiles of Ross-Miles foam height vs. time shown in Table 5 indicate that Formulation 8 (containing the IPM pre-thickened by Geahlene) presents lather volume and lather stability comparable to those of Formulation 6 (surfactant-base w/o oil). In contrast, Formulation 9 (IPM alone w/o Geahlene thickening) may destabilize the foam (i.e., less lather volume and foam texture is thin) as the aging time was longer than 6 minutes.

TABLE 5

Ross-Miles Foam Height as a Function of Foam Aging For Cleansers Containing the Polymer/Oil Thickening Compositions and Non-thickened Oil

| Foam Aging Time (minutes) | Foam Height (cm) Formulation No. 6 (surfactant base) | Foam Height (cm) Formulation No. 8 (invention) | Foam Height (cm) Formulation No. 9 (comparative) |
| --- | --- | --- | --- |
| 0.8 | 18 | 18 | 17 |
| 1.7 | 17 | 18 | 17 |
| 2.5 | 17 | 18 | 16 |
| 4.1 | 17 | 17 | 16 |
| 6.2 | 16 | 17 | 15 (also formed thin foam, not desired) |
| 8.0 | 16 | 17 | 13 (thin foam) |
| 9.4 | 16 | 16 | 12 (thin foam) |
| 10 | 16 | 16 | 12 (thin foam) |
| 12 | 16 (still creamy foam, desired) | 16 (still creamy foam, desired) | 10 (thin foam) |

Example 6
Aqueous Skin Cleansers Containing Polydimethylsiloxane (PDMS) Thickened Oils An isopropyl myristate (IPM, viscosity at about 10 cp) and a polydimethylsiloxane (PDMS, viscosity around 60,000 cp) were pre-mixed in 1:1 weight ratio at 20° C. using a overhead mixer for 30 minutes. The resulting IPM/PDMS thickening composition (a preferred example of the subject invention) has a viscosity that is more than ten times higher than that of isopropyl myristate alone. By using the preparation method shown in Example 6–8, including the thickened siloxane/IPM thickening composition in a skin cleanser base (Formulation No. 10) resulted in a pourable, creamy white viscous liquid (Formulation No. 11).

Under the same pre-mixing condition, a PDMS (viscosity at about 60,000 cp)/sunflower oil (viscosity at about 10 cp) was prepared. The resulting PDMS/sunflower seed oil thickening composition (a preferred example of the subject invention) has a viscosity that is more than ten times higher than that of sunflower oil alone. By the preparation method shown in Example 6 to 8, including the PDMS/sunflower seed oil thickening composition in a skin cleanser base (Formulation No. 10) resulted in a pourable, creamy white viscous liquid (Formulation 12).

For the comparison purpose, IPM/Aluminum Stearate (a crystalline thickener, non-preferred by the subject invention) in 9:1 weight ratio were mixed and heated to 120° C. to form a clear gel. Cooling the gel down to 20° C. resulted in a hazy viscous gel. By the preparation method shown in Example 6 to 8, including this Al Stearate/IPM thickening composition in a skin cleanser (Formulation 10) resulted in a creamy, pourable viscous liquid (Formulation 13).

Formulation No. 10 to No. 13

| Materials | Formulation No.10 (base) | Formulation No.11 (invention) | Formulation No.12 (invention) | Formulation No.13 (comparative) |
|---|---|---|---|---|
| sodium cocoyl isethionate | 4.2% | 4.2% | 0 | 0 |
| cocoamido propyl betaine | 8.3% | 8.3% | 0 | 0 |
| sodium laurylether sulfate (3EO) | 4.2% | 4.2% | 0 | 0 |
| 1:1 w/w IPM/ PDMS | 0 | 16.6% | 0 | 0 |
| 1:1 w/w sunflower seed oil/PDMS | 0 | 0 | 16.6% | 0 |
| 1:9 w/w Aluminum stearate/IPM | 0 | 0 | 0 | 16.6% |
| water | to 100% by wt. | to 100% by wt. | to 100% by wt. | to 100% by wt. |

As shown in Table 6, the lather performance of Formulation No. 11 and No. 12 is significantly better than Formulation No. 13, which contains isopropyl myristate thickened by Al Stearate, a crystalline material. The results in this example indicate that the conventional thickening agents, such as Al stearate (a long chain insoluble fatty acid soap), can seriously antifoam in the presence of the oil. In contrast, PDMS, a non-crystalline hydrophobic polymer can thicken an oil w/o sacrificing the lather performance of an aqueous cleanser.

TABLE 6

Comparison of the lather volume of Formulation No.11–No.13.

| Formulation | Lather Volume (ml) generated from the Cylinder-shaking Method |
|---|---|
| No. 11 | 172 |
| No. 12 | 181 |
| No. 13 | 117 |

Example 7
Aqueous Skin Cleansers Containing Petrolatum Thickened Oils

An isopropyl myristate (IPM, viscosity at about 10 cp) and a Petrolatum (from Fisher Scientific) were pre-mixed in 1:1 weight ratio at 20° C. using a overhead mixer for 30 minutes. The resulting IPM/petrolatum thickening composition (a preferred example of the subject invention) has a viscosity that is more than ten times higher than that of isopropyl myristate alone. By using the preparation method shown in Example 2, including the thickened siloxane/IPM thickening composition in a skin cleanser base (Formulation No. 10) resulted in a pourable, creamy white viscous liquid (Formulation No. 14).

For the comparison purpose, IPM/paraffin wax (a crystalline thickener, non-preferred by the subject invention) in 1:1 weight ratio were mixed and heated to 120° C. to form a clear gel. Cooling the gel down to 20° C. resulted in a hazy viscous gel. By the preparation method shown in Example 2, including this paraffin/IPM thickening composition in a skin cleanser base (Formulation No. 10) resulted in a pourable viscous liquid (Formulation No. 15).

Formulation No. 14 and No. 15

| Materials | Formulation No.14 (invention) | Formulation No.15 (comparative) |
|---|---|---|
| sodium cocoyl isethionate | 4.2% | 4.2% |
| cocoamido propyl betaine | 8.3% | 8.3% |
| sodium laurylether sulfate (3EO) | 4.2% | 4.2% |
| pre-thickened 1:1 w/w IPM/ Petrolatum (invention) | 16.7% | 0 |
| pre-thickened 1:1 w/w IPM/ Paraffin wax (comparative) | 0 | 16.7% |
| water | to 100% by wt. | to 100% by wt. |

As shown in Table 7, the lather performance of Formulation No. 14 (invention) is better than that of formulation No. 10 (base) and is significantly better than Formulation No. 15 (comparative), which contains isopropyl myristate thickened by paraffin wax, a crystalline thickening material. The results in this example indicate that the conventional crystalline thickening agents, such as paraffin wax, can seriously antifoam in the presence of the oil. In contrast, petrolatum, a microcrystalline hydrophobic polymer can thicken an oil w/o sacrificing the lather performance of an aqueous cleanser.

TABLE 7

Comparison of the lather volume of Formulation No.10, No.14 and No.15.

| Formulation | Lather Volume (ml) generated from the Cylinder-shaking Method |
|---|---|
| No. 10 | 167 (cleanser base) |
| No. 14 | 190 (invention) |
| No. 15 | 93 (comparative) |

Example 8
Large Droplet Size and Stability of Geahlene Oils in Shower Gels

The optical microscopy study showed that Geahlene® 1600 may form more stable, larger oil droplets in a cleanser in comparison to those non-thickened oil alone in the cleanser. Such high viscosity, larger size oil droplets are generally desired for the purpose of the deposition by the target oil onto the skin (see, for example, World Patent Nos. WO 94/01084 and WO 94/01085).

Applicants prepared a micrograph showing the oil droplets of 16.7% Geahlene® 1600 in an aqueous based formulation containing 8.3% cocoamidopropyl betaine, 4.2% sodium laureth sulfate (3EO) and 4.2% sodium cocoyl isethionate. The non-spherical shapes of some of the oil droplets may be indicative of the high viscosity of the Geahlene, which is desired for the purpose of skin deposition.

In contrast, 16.7% non-thickened isopropylmyristate (IPM) tend to dramatically thin the same base formulation and tend to phase separate from the bulk aqueous phase (i.e., a few hours after the sample was prepared). As a result of this instability, very little amount of IPM can be homogeneously dispersed and stabilized in the base formulation. Also, the thinning caused by the addition of IPM made the formulation unsuitable for personal washing applications.

We claim:

1. A liquid skin cleansing composition comprising
    (a) about 10% to 50% by wt. of a surfactant selected from the group consisting of anionic surfactants, cationic surfactants, amphoteric surfactants, nonionic surfactants and mixtures thereof; and
    (b) 0.5% to 30% by wt. total composition a pre-thickened oil composition with a viscosity greater than 2000 centipoise (cp),
    wherein said specific pre-thickened oil composition (b) comprises (i) a hydrophobic emollient agent having a viscosity less than 1000 cp and (ii) a polymeric thickener compound; wherein the cleansing composition containing said polymer/oil thickening composition (b) provides a foam height of at least seven cm or greater after two minutes of foam aging, as tested by the Ross-Miles method,
    wherein said thickener is selected such that:
        (I) the hydrophobicity of the polymeric thickener is such that it has a solubility less than 1% by wt. when measured in water at 25° C.;
        (II) oil miscibility or/and dispersibility of the thickener is such that, upon mixing with the said low viscosity oil b(i), the polymer/oil thickening composition which forms is a homogeneously thickened oil having a viscosity greater than 2000 cp, and which does not have layer separation;
        (III) the content of crystalline materials in the thickener is less than 20% by wt., and the content of materials, selected from the group consisting of non-crystalline gels, non-crystalline amorphous solids and microcrystalline waxes, in the thickener is greater than 80% by wt.

2. A composition according to claim 1, wherein (b)(i) is selected from the group consisting of mineral oil, isopropyl myristate, isopropyl palmitate, silicones, benzoate esters, and mixtures thereof, and the thickening agent (b)(ii) is a blend of at least two different polymer members selected from the group consisting of diblock copolymers, triblock copolymers, radial block copolymers and multiblock copolymers, with the proviso that there be contained in the composition at least one diblock copolymer or at least one triblock copolymer, with said at least one diblock copolymer or said at least one triblock copolymer comprising 5 to 95 wt. % of said blend of at least two different polymers, said diblock and triblock polymers comprising segments of styrene monomer units and rubber monomer units.

3. A composition according to claim 1, wherein (b)(i) comprises 10% to 90% by wt. of a silicone soluble hydrophobic emollient agent with viscosity less than 1000 cp selected from the group consisting of diisopropyl sebacate, octyl isononanoate, isodecyl octanoate, diethylene glycol, isopropyl myristate, isocetyl palmitate, isopropyl isostearate, isocetyl palmitate, isostearyl palmitate, diisostearyl malate, diglyceryl isostearate, diisopropyl dimerate, diglyceryl diisostearate, and mixtures thereof; and (b)(ii) comprises 10% to 90% by wt. silicone oil having viscosity greater than 2000.

4. A composition according to claim 3, wherein the said silicone oil has a viscosity greater than 5,000 cp.

5. A composition according to claim 3, wherein the said silicone oil has a viscosity greater than 10,000 cp.

6. A composition according to claim 1, wherein (b)(i) comprises 5% to 80% by wt. a hydrophobic emollient agent with a viscosity less than 1000 cp selected from the group that are silicone mixable and dispersable consisting of mineral oil, lanolin oil, coconut oil, jojoba oil, maleated soybean oil, castor oil, almond oil, peanut oil, wheat germ oil, rice bran oil, linseed oil, apricot pits oil, walnuts, palm nuts, pistachio nuts, sesame seeds, rape seed oil, cade oil, corn oil, peach pit oil, poppyseed oil, pine oil, soybean oil, avocado oil, sunflower seed oil, hazelnut oil, olive oil, grapeseed oil, and safflower oil, babassu oil, and mixtures thereof; and (b)(ii) comprises 20% to 95% by wt. silicone oil having a viscosity greater than 2000 cp.

7. A composition according to claim 6, wherein said silicone oil has a viscosity greater than 10,000 cp.

8. A composition according to claim 6, wherein (b)(i) comprises 20% to 60% by wt. of the composition (b)(ii) comprises 40% to 80% by wt. of the composition and (b)(ii) has a viscosity greater than 10,000 cp.

9. A composition according to claim 1, wherein (b)(i) comprises a hydrophobic emollient agent with viscosity less than 1000 cp selected from the group consisting of mineral oil, sorbitol, lanolin oil, coconut oil, jojoba oil, maleated soybean oil, castor oil, almond oil, peanut oil, wheat germ oil, rice bran oil, linseed oil, apricot pits oil, walnuts, palm nuts, pistachio nuts, sesame seeds, rape seed oil, cade oil, corn oil, peach pit oil, poppyseed oil, pine oil, soybean oil, avocado oil, sunflower seed oil, hazelnut oil, olive oil, grapeseed oil, and safflower oil, Shea butter, babassu oil, isopropyl myristate and mixtures thereof; and (b)(ii) comprises 10% to 80% by wt. microcrystalline waxes having viscosity greater than 2000 cp.

10. A composition according to claim 9, wherein the microcrystalline wax is petrolatum having a viscosity greater than 10,000 cp.

11. A composition according to claim 1, wherein the skin cleansing composition comprises 10% to 30% by wt. of a surfactant selected from the group consisting of anionic surfactants, cationic surfactants, amphoteric surfactants, nonionic surfactants and mixtures thereof.

12. A composition according to claim 1, wherein the skin cleansing composition further comprises 0 to 25% by wt. of an ingredient selected from the group consisting of organic solvents; auxiliary thickeners; perfumes; sequestering agents and coloring agents, opacifiers and pearlizers.

13. A composition according to claim 12, wherein the solvent is ethanol.

14. A composition according to claim 12, wherein the thickener is selected from the group consisting of carboxymethylcellulose, magnesium aluminum silicate, hydroxymethylcellulose, methylcellulose, carbopol; glucamide and mixtures thereof.

15. A composition according to claim 12, wherein the sequestering agent is 0.01 to 1% tetrasodium ethylenediaminetetraacetate (EDTA), EHPP or mixtures thereof.

16. A composition according to claim 12, wherein the pearlizer is selected from the group consisting of zinc stearate, magnesium stearate, $TiO_2$, ethylene glycol monostearate and styrene/acrylate copolymers.

17. A composition according to claim 1, wherein the composition further comprises 0 to 5% by wt. antimicrobials or preservatives.

18. A composition according to claim 17, wherein the antimicrobial is 2-hydroxy-4,2',4' trichlorodiphenylether.

19. A composition according to claim 17, wherein the preservative is selected from the group consisting of dimethyloldimethylhydantoin, parabens and sorbic acid.

20. A composition according to claim 1, wherein the composition further comprises coconut acyl, mono- or diethanol amides and ionizing salts.

21. A composition according to claim 20, wherein ionizing salt is sodium chloride or sodium sulfate.

22. A composition according to claim 1, wherein the composition further comprises 0 to 3% by wt. antioxidants.

23. A composition according to claim 22, wherein the antioxidant comprises 0.01 and higher butylated hydroxytoluene (BHT).

24. A composition according to claim 1, wherein the composition further comprises 0 to 5% by wt. cationic conditioners.

25. A composition according to claim 1, wherein the composition further comprises 0 to 10% by wt. nonionic polyethylene glycols having a molecular weight between 200 and 20,000 Dalton.

26. A composition according to claim 1, wherein the composition further comprises exfoliants.

27. A composition according to claim 26, wherein exfoliants are selected from the group consisting of polyoxyethylene beads, walnut shells and apricot seeds.

28. A composition according to claim 1, wherein the composition further comprises 0.1 to 15% by wt. of a saturated or unsaturated, branched or unbranched $C_8$–$C_{24}$ liquid fatty acid structurant or ester derivative thereof; saturated or unsaturated, branched or unbranched $C_8$–$C_{24}$ liquid alcohol or ether derivatives thereof.

29. A composition according to claim 28, wherein the structurant is selected from the group consisting of capric acid or caprylic acid, oleic acid, isostearic acid, linoleic acid, linolenic acid, ricinoleic acid, elaidic acid, arichidonic acid, myristoleic acid and palmitoleic acid, propylene glycol isostearate, propylene glycol oleate, glyceryl isostearate, glyceryl oleate and polyglyceryl diisostearate, oleyl alcohol, isostearyl alcohol, isosteareth or oleth carboxylic acid, isosteareth or oleth alcohol; and wherein the structuring agent has a melting point below about 25° C. centigrade.

30. A composition according to claim 1, wherein the pre-thickened oil composition has a viscosity greater than 5,000 cp.

31. A composition according to claim 1, wherein the pre-thickened oil composition has a viscosity greater than 10,000 cp.

32. A composition according to claim 1, wherein said liquid skin cleansing composition contains 5% to 25% by wt. of said pre-thickened oil composition.

33. A composition according to claim 1, wherein said liquid skin cleansing composition containing said pre-thickened oil provides a foam height that is at least 30% greater than that provided by a comparative liquid composition containing the same percentage of the same low viscosity oil (viscosity less than 1000 cp) which has been pre-thickened by crystalline thickeners, selected from polyethylene or paraffin waxes, $C_{18}$–$C_{22}$ fatty acid soap and fumed silica, as tested by the Ross-Miles method after two minutes of foam ageing.

* * * * *